(12) United States Patent
Baishya et al.

(10) Patent No.: US 8,841,466 B2
(45) Date of Patent: Sep. 23, 2014

(54) SERIES OF ARTEMISININ DERIVATIVES AND PROCESS FOR PREPARATION THEREOF

(75) Inventors: Gakul Baishya, Assam (IN); Nabin Chandra Barua, Assam (IN); Abhishek Goswami, Assam (IN); Partha Pratim Saikia, Assam (IN); Paruchuri Gangadhar Rao, Assam (IN); Ajit Kumar Saxena, Jammu-Tawi (IN); Nitasha Suri, Jammu-Tawi (IN); Madhunika Sharma, Jammu-Tawi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/574,440

(22) PCT Filed: Jan. 20, 2011

(86) PCT No.: PCT/IB2011/000078
§ 371 (c)(1),
(2), (4) Date: Oct. 15, 2012

(87) PCT Pub. No.: WO2011/089507
PCT Pub. Date: Jul. 28, 2011

(65) Prior Publication Data
US 2013/0030044 A1    Jan. 31, 2013

(30) Foreign Application Priority Data

Jan. 22, 2010 (IN) .............................. 127/DEL/2010

(51) Int. Cl.
*C07D 321/00* (2006.01)

(52) U.S. Cl.
USPC .......................................................... 549/348

(58) Field of Classification Search
USPC ........................................................... 549/348
See application file for complete search history.

(56) References Cited

U.S. PATENT DOCUMENTS 6,156,790 A * 12/2000 Posner et al. .................. 514/450

OTHER PUBLICATIONS

International Search Report of PCT/IB2011/000078, Apr. 21, 2011.

* cited by examiner

*Primary Examiner* — Nizal Chandrakumar
(74) *Attorney, Agent, or Firm* — Edwards Wildman Palmer LLP; Jeffrey D. Hsi

(57) ABSTRACT

This invention relates to the synthesis of certain novel Baylis-Hillman adducts of artremisinin derived aldehyde 2-[10'β-deoxoartemisininyl]-ethanal. The capabilities of introduction of three functional groups into a molecule in one step using Baylis-Hillman reaction encouraged us to synthesize some highly functionalized derivatives of artemisinin. These highly functionalized artemisinin derivatives embodied in this document are found to be active against various cancer cell-lines.

9 Claims, 2 Drawing Sheets

Compound 3a (α-OH), R = methyl 2-acrylate
Compound 3b (α-OH) and 3b' (β-OH), R = 2-acrylonitrile
Compound 3c (α-OH), R = methyl 2-vinylketone
Compound 3d (α-OH), R = 2-cyclohexenone
Compound 3e (α-OH) and 3e' (β-OH), R = 2-cyclopentenone

Scheme 1.

10-Deoxoallylartemisinin

Scheme 2.

Compound 3a (α-OH), R = methyl 2-acrylate
Compound 3b (α-OH) and 3b' (β-OH), R = 2-acrylonitrile
Compound 3c (α-OH), R = methyl 2-vinylketone
Compound 3d (α-OH), R = 2-cyclohexenone
Compound 3e (α-OH) and 3e' (β-OH), R = 2-cyclopentenone

SERIES OF ARTEMISININ DERIVATIVES AND PROCESS FOR PREPARATION THEREOF

CROSS REFERENCE TO RELATED APPLICATIONS

This application is the national phase under 35 U.S.C. §371 of PCT International Application No. PCT/IB2011/000078, filed Jan. 20, 2011, which claims the benefit of Indian Patent Application No. 172/DEL/2010, filed Jan. 22, 2010, the entire contents of the aforementioned applications are hereby incorporated herein by reference.

FIELD OF THE INVENTION

The invention relates to a series of artemisinin derivatives and process for preparation thereof. The invention particularly relates to a series of novel highly functionalized Baylis-Hilmann adducts of artemisinin derived aldehyde showing strong anticancer activities and process for their preparation.

BACKGROUND OF THE INVENTION

Malaria parasite developed themselves as resistant to a variety of anti-malarial drugs which matters as a strong challenge to medicinal chemists to develop and search for new anti-malarial drugs.

The compound artemisinin, also known as Qinghaosu (QHS), isolated in 1971 from the Chinese medicinal plant *Artemisia annua* is inexpensive and used as traditional chinese medicine against malaria.

Artemisinin and its simple derivatives artemether, arteether and sodium artesunate have gained importance over the years as a new generation of antimalarial drugs, especially in the treatment of multi-drug-resistant malaria strains. However these 'first generation' derivatives suffer from poor oral bioavailability and short plasmatic half-life.

Replacement of the oxygen at the C-10 position with carbon could be expected to produce compounds i.e. so-called 'second generation' compounds not only with greater hydrolytic stability but also with a longer half life and potentially lower toxicity. Consequently several groups have developed synthetic and semi-synthetic approaches to C-10 carba-analogues of artemisinin (*J. Med. Chem.* 1999, 42, 5487; ibid 2000, 43, 4228; *Tetrahedron*, 1999, 55, 3625; *Bioorg. Med. Chem. Lett* 2005, 15, 2629; U.S. Pat. No. 5,142,328, Mexican patent 236235, 2006).

In addition to this antimalarial activity, it has been shown that some artemisinin derivatives and dimers have anti-cancer properties (*J. Med. Chem.* 2003, 46, 987-994; U.S. Pat. No. 6,790,863; U.S. Pat. No. 5,677,468).

Over the past twenty years only a few drugs isolated from higher plants have yielded clinical agents, the outstanding examples being vinblastine and vincristine from the *Madagascan periwinkle*, *Catharanthus roseus*, etoposide, the semi-synthetic lignam, from May-apple *Podophyllum peltatum* and the diterpenoid taxol, commonly referred to as paclitaxel, from the Pacific yew, *Taxus brevifolia*. Of these agents, paclitaxel is the most exciting, recently receiving approval from the United States Food and Drug Administration for the treatment of refractory ovarian cancer. Since the isolation of artemisinin, there has been a concerted effort by investigators to study other therapeutic applications of artemisinin and its derivatives.

National Institutes of Health reported that artemisinin is inactive against P388 leukemia (See NCI Report on NSC 369397 tested on 25 Oct. 1983). Later anticancer studies that have been conducted on cell line panels consisting of 60 lines organized into nine, disease-related subpanels including leukemia, non-small-cell lung cancer, colon, CNS, melanoma, ovarian renal, prostate and breast cancers, further confirm that artemisinin displays very little anticancer activity. A series of artemisinin-related endoperoxides were tested for cytotoxicity to Ehrlich ascites tumor (EAT) cells using the microculture tetrazolum (MTT) assay (H. J. Woerdenbag, et al. "Cytotoxicity of Artemisinin-Related Endoperoxides to Ehrlich Ascites Tumor Cells," *Journal of Natural Products* 1993, 56 (6), 849-856). The MTT assay, used to test the artemisinin-related endoperoxides for cytotoxicity, is based on the metabolic reduction of soluble tetrazolium salts into insoluble colored formazan products by mitochondrial dehydrogenase activity of the tumor cells. As parameters for cytotoxicity, the $IC_{50}$ and $IC_{80}$ values, the drug concentrations causing respectively 50% and 80% growth inhibition of the tumor cells, were used. Artemisinin, had an $IC_{50}$ value of 29.8 µM. Derivatives of dihydroartemisinin (DHA) being developed as antimalarial drugs (artemether, arteether, sodium artesunate, artelinic acid and sodium artelinate), exhibited a somewhat more potent cytotoxicity. Their $IC_{50}$ values ranged from 12.2 µM to 19.9 µM. The DHA condensation by-product, disclosed previously by M. Cao, et al., 1984, was the most potent cytotoxic agent, its $IC_{50}$ being 1.4 µM. At this drug concentration the condensation by-product, is approximately twenty-two times more cytotoxic than artemisinin and sixty times more cytotoxic than DHA. There is still a need, therefore, for developing structural analogs of artemisinin as antitumor agents that have potency equivalent or greater than known anticancer agents.

SUMMARY OF THE PRESENT INVENTION

Accordingly, the present invention provides a compound of general formula 3

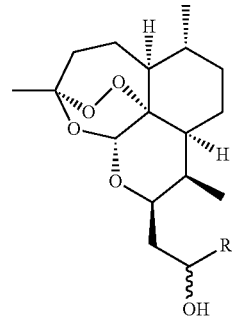

General formula 3 wherein R is selected from 2-acrylic ester wherein the ester group is selected from methyl, ethyl, i-propyl, t-butyl, aryl, 2-acrylonitrile, alkyl vinyl keto group wherein the alkyl group is selected from methyl, ethyl, propyl, 2-cyclic enone moiety with the ring size of five, six, seven membered.

In an embodiment of the invention wherein the representative compounds of general formula 3 comprising the structural formula 3a to 3e:

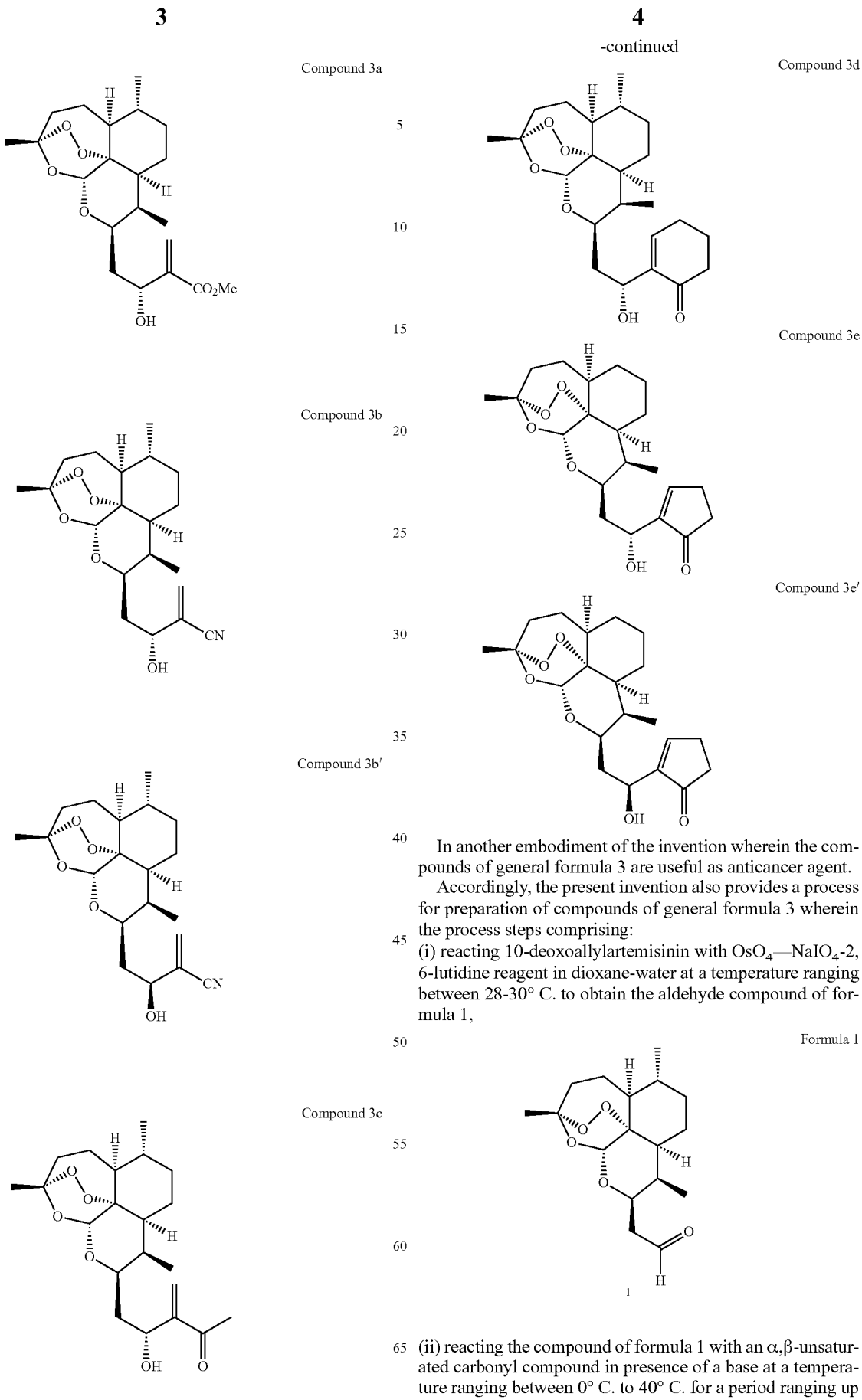

In another embodiment of the invention wherein the compounds of general formula 3 are useful as anticancer agent.

Accordingly, the present invention also provides a process for preparation of compounds of general formula 3 wherein the process steps comprising:

(i) reacting 10-deoxoallylartemisinin with $OsO_4$—$NaIO_4$-2,6-lutidine reagent in dioxane-water at a temperature ranging between 28-30° C. to obtain the aldehyde compound of formula 1, (ii) reacting the compound of formula 1 with an α,β-unsaturated carbonyl compound in presence of a base at a temperature ranging between 0° C. to 40° C. for a period ranging up to 3 days, purifying the desired compound of general formula 3 using the chromatographic methods.

In an embodiment of the invention wherein the α,β-unsaturated carbonyl compound may be selected from a group consisting of methyl acrylate, acrylonitrile, methyl vinyl ketone, 2-cyclohexenone, 2-cyclopentenone.

In another embodiment of the invention wherein the base may be selected from a group consisting of 1,4-diazabicyclo [2.2.2]octane, imidazole, 4-(N,N-dimethylamino)-pyridine wherein imidazole is used in combination of L-proline as a co-catalyst.

In yet another embodiment of the invention wherein the reaction can be carried out in absence of solvent or may be carried out in presence of a solvent selected from a group consisting of dimethyl formamide, THF (tetrahydrofuran)-water and the like.

In still another embodiment of the invention wherein the chromatographic method for purification of the compounds is selected from column chromatography over silica gel of 100-200 mesh and preparative thin layer chromatography (TLC) using silica gel of TLC grade. The solvent ethyl acetate and hexane have been used as eluents for column chromatography and thin layer chromatography (TLC).

In one of the feature of the present invention, the compound of general formula 1, used for the preparation of compound of general formula 3 has been synthesized in a single step process for the first time using $OsO_4$—$NaIO_4$-lutidine reagent system in dioxane-water mixture In still another embodiment of the invention wherein the compounds may be used for preparation of a pharmaceutical composition comprising an effective amount of at least one compound of general formula 3 along with the pharmaceutically acceptable carrier, diluent or excepients.

BRIEF DESCRIPTION OF THE DRAWINGS

The present invention is further described below with reference to the following non-limiting examples and with reference to the following figures, in which.

DETAILED DESCRIPTION OF THE PRESENT INVENTION

Figure 1:
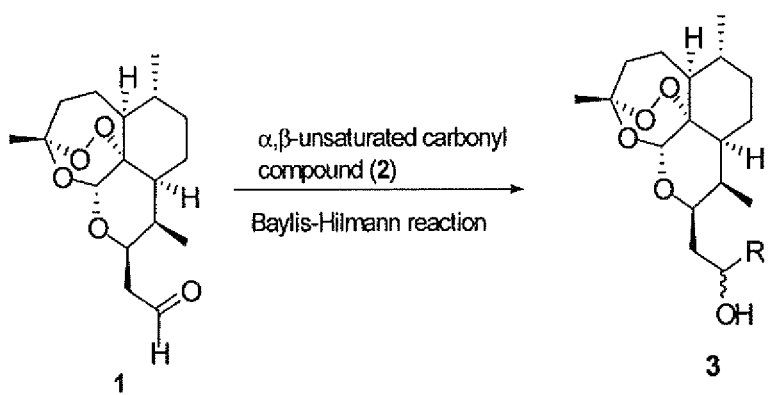
FIG. 1. depicts a process for the preparation of compounds of formula 3 by treatment of artemisinin derived aldehyde with different α,β-unsaturated carbonyl compounds.
Figure 2:
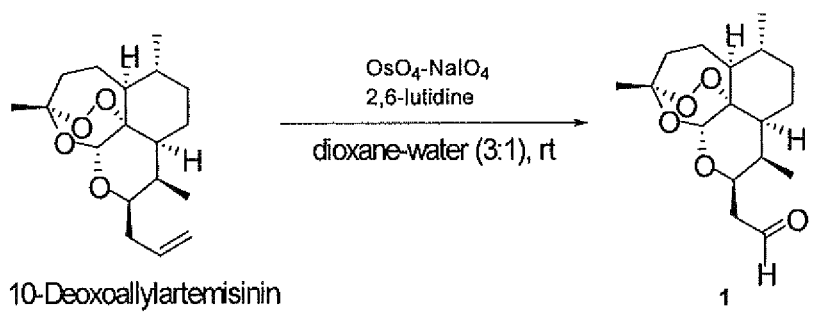
FIG. 2. depicts the preparation of aldehyde 1 (Scheme 1) and the preparation of compounds of formula 3 by treatment of artemisinin derived aldehyde with different α,β-unsaturated carbonyl compounds (Scheme 2).
Figure 2:
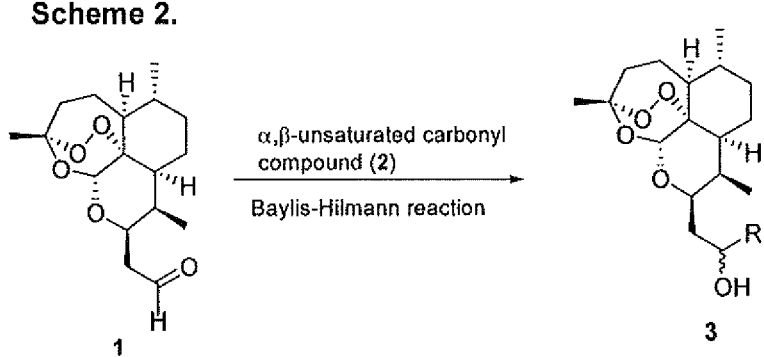

The invention relates to a development of series of novel highly functionalized adducts of artemisinin derived aldehyde 2-[10'β-deoxoartemisininyl]-ethanal 1 showing strong anticancer activities and processes for their preparation.

The problem which the present invention proposes to solve is to obtain novel derivatives of artemisinin having anticancer activities.

Due to the poor bioavailability and stability of C-10 oxa analogues of artemisinin, the invention also focuses on the second generation derivatives of artemisinin using C-10 deoxoartemisinin.

Different functionalized derivatives of C-10 deoxoartemisinin have been prepared by the inventors in order to slow down the various processes of the metabolism (oxidation, hydrolysis and glucuronidation) which take place on C-10 carbon and thus to prolong the duration of the action of artemisinin derivatives.

The known aldehyde 1 derived from artemisinin has been utilized to provide some novel C-10 deoxo artemisinin compounds.

Highly functionalized derivatives of artemisinin have been synthesized from the known aldehyde 1 using some known reactions such as Baylis-Hillman reaction and the like.

Reactions of the artemisinin derived aldehyde 1 with different α,β-unsaturated carbonyl compounds have been performed under different reaction condition.

The present invention follows on from the highlighting by the inventors that it is possible to prepare new artemisinin derivatives performing Baylis-Hillman reaction and the like with the known aldehyde 1 derived from artemisinin, which has proved to extend the period of action of artemisinin.

The present invention has consisted of finding chemical means of introducing three functional groups into the artemisinin molecule with the removal of neurotoxic C-10 oxygen.

The known aldehyde 1 has been obtained from the 10-deoxoallylartemisinin in one step using $OsO_4$—$NaIO_4$-lutidine reagent system in dioxane-water mixture. The compounds of formula 3 wherein the functional moiety R represents different α,β-unsaturated carbonyl fragment; R represents methyl acrylate, ethyl acrylate, t-butyl acrylate or aryl acrylate and the like; R represents acrylonitrile; R represents methyl vinyl ketone; R represents 2-cyclohexenone; R represents 2-cyclopentenone.

The products of formula 3 exist in the form of diastereomers. The ratios of diastereomeric mixtures vary in each case.

The absolute stereochemistries of the products were not determined, but the major less polar isomer can be arbitrarily designated as α-diastereomer and the minor more polar compound as the β-diastereomer according to the literature reported by Ma et al. (*J. Med. Chem.* 2000, 43, 4228) where they also arbitrarily designated the stereochemistries of 2°-alcohols obtained from the reaction of the aldehyde 1 with different Grignard reagents.

The present invention also provides that the compound of the general formula is active against various cancer cell-lines.

The invention also provide the compound of the general formula 3 where R=methyl vinyl ketone is showing strong activities against all cancer cell examined here than other compounds.

The compound of the formula where R represents methyl vinyl ketone is preferably given more importance due to its highest anti-cancer activities.

The invention also relates to a solvent-free process in case of the preparation of the compound of the general formula where R represents acrylic ester or acrylonitrile.

In this invention, it was proved for the first time that the 1,2,3-trioxane ring system is stable under different Baylis-Hillman reaction conditions. Hence this reaction can also be performed with other aldehydes that can be synthesized through different routes from the artemisinin molecule at different carbon positions.

In accordance with the present invention, the starting aldehyde 1 was prepared according to conventional methods of organic chemistry. This is illustrated in Schemes 1, in which the starting materials and reagents, when their mode of preparation is not described, are commercially available or is described in the literature or may be prepared according to methods which are described therein or which are known to persons skilled in art.

The invention also relates to a process for the preparation of compounds of formula 3 defined above, characterized in that it comprises a treatment of artemisinin derived aldehyde with different α,β-unsaturated carbonyl compounds under different reaction conditions (Scheme 2).

Reaction of the known aldehyde 1 with acrylonitile under solvent-free condition is more yielding than reactions with other α,β-unsaturated carbonyl compounds.

The invention will be further illustrated using the detailed description of new artemisinin derivatives, and their properties and should not construed the scope of the invention.

In vitro cytotoxicity against human cancer cell lines:

The human cancer cell lines procured from National Cancer Institute, Frederick, U.S.A., were used in present study. Cells were grown in tissue culture flasks in complete growth medium (RPMI-1640 medium with 2 mM glutamine, 100 μg/mL streptomycin, pH 7.4, sterilized by filtration and supplemented with 10% fetal bovine serum and 100 units/ml penicillin before use) at 37° C. in an atmosphere of 5% $CO_2$ and 90% relative humidity in a carbon dioxide incubator. The cells at subconfluent stage were harvested from the flask by treatment with trypsin (0.05% in PBS containing 0.02% EDTA) for determination of cytotoxicity. The cell suspension of the required cell density was prepared in complete growth medium with gentamycin (50 μg/mL) for determination of cytotoxicity.

Stock solutions of $2\times10^{-2}$ M of test materials were prepared in DMSO. The stock solutions were serially diluted with complete growth medium containing 50 μg/ml of gentamycin to obtain working test solution of $2\times10^{-5}$ M to obtain final concentration of $1\times10^{-5}$ M respectively.

In vitro cytotoxicity against human cancer cell lines was determined (Monks of al., *J. Natl. Cancer Inst.* 1991, 83, 757-766). The 100 μL of cell suspension was added to each well of the 96-well tissue culture plate. The cells were incubated for 24 hours (at 37° C. in an atmosphere of 5% $CO_2$ and 90% relative humidity in a carbon dioxide incubator). Test materials in complete growth medium (100 μL) were added after 24 hours incubation to the wells containing cells. The plates were further incubated for 48 hours in a carbon dioxide incubator after addition of test material. The cell growth was stopped by gently layering trichloroacetic acid (50 μL, 50% w/v) on top of the medium in all the wells. The plates were incubated at 4° C. for one hour to fix the cells attached to the bottom of the wells. The liquid of all the wells was then gently decanted and discarded. The plates were washed five times with distilled water and air-dried. Cell growth was measured by staining with sulforhodamine B dye (Skehan et al., *J. Natl. Cancer Inst.* 1990, 82, 1107-1112). The adsorbed dye was dissolved in Tris-Buffer (100 μL, 0.01M, pH 10.4) and plates were gently stirred for 10 minutes on a mechanical stirrer. The optical density (OD) was recorded on ELISA reader at 540 nm.

The cell growth was calculated by subtracting mean OD value of respective blank from the mean OD value of experimental set. Percent growth in presence of test material was calculated considering the growth in absence of any test material as 100% and in turn percent growth inhibition in presence of test material was calculated. Suitable blank, controls and positive controls were included in the study.

All compounds reported here have been tested for in vitro anticancer activity against seven cancer cell lines and some of them have shown extraordinary encouraging results. Compound 3c showed 100% growth inhibition (% GI) against colon colo-205 human cancer cell line. Similarly the same compound has also been found promising with 85% GI against Lung cancer cell line A-549 which is comparable with paclitaxel (GI 69% at $1\times10^{-5}$ M concentration). Among other compounds, the compound 3b' showed glimpses of good activity (GI 78%) against human prostate cell line of PC-3 type which is comparable with that of compound 3c (GI 81%). Among all these compounds discussed herein, compound 3c has been found to possess activity against almost all seven cancer cell lines tested in this study. In the Table 1, it is clearly mentioned that the % GI values of all novel artemisinin derivatives against various cancer cell lines are much better than artemisinin itself. In some cases the % GI values are comparable with known anti cancer drugs.

For example, the known anti cancer drug 5-fluorouracil is showing 54% GI at $2\times10^{-5}$ M concentration against colon cancer cell lines colo-205 where as the compound 3b' and 3c showing 75% and 100% GI respectively. Again, the % GI value of mytomycin against prostate cancer cell lines PC-3 is 54 at $1\times10^{-5}$ M concentration where as the % GI values of 3b, 3b', 3d, 3e, 3e' and 3c are 65, 78, 68, 71, 71 and 81 respectively at $5\times10^{-5}$ M concentration. The in vitro anticancer activity results are summarized in Table 1.

TABLE 1

In vitro anticancer activity.

| Compound | Conc (M) | Lung A-549 | Ovary IGR-OV-1 | Prostate DU-145 | Prostate PC-3 | Neuroblastoma IMR-32 | Breast MCF-7 | Colon Colo-205 |
|---|---|---|---|---|---|---|---|---|
| | | | | % GROWTH INHIBITION | | | | |
| 3a | $5 \times 10^{-5}$ | 70 | 63 | — | — | 56 | — | — |
| 3b | $5 \times 10^{-5}$ | 66 | 42 | 46 | 65 | 48 | 46 | 56 |
| 3b' | $5 \times 10^{-5}$ | 77 | 56 | 60 | 78 | 62 | 55 | 75 |
| 3d | $5 \times 10^{-5}$ | 66 | 60 | 52 | 68 | 72 | 43 | 63 |
| 3e | $5 \times 10^{-5}$ | 68 | 54 | 47 | 71 | 66 | 51 | 63 |
| 3e' | $5 \times 10^{-5}$ | 70 | 52 | 41 | 71 | 57 | 40 | 50 |
| 3c | $5 \times 10^{-5}$ | 85 | 33 | 73 | 81 | 79 | 66 | 100 |
| Artemisinin | $5 \times 10^{-5}$ | 29 | 26 | 38 | 22 | 23 | 34 | 40 |
| 5-Fluorouracil | $2 \times 10^{-5}$ | — | — | — | — | — | — | 54 |
| Paclitaxel | $1 \times 10^{-5}$ | 69 | — | — | — | — | — | — |
| Mitomycin | $1 \times 10^{-5}$ | — | — | 92 | 54 | — | — | — |
| Adriamycin | $1 \times 10^{-6}$ | — | — | — | — | 70 | 72 | — |

$^1$H NMR and $^{13}$C NMR spectra were recorded using a Bruker DPX-300 NMR machine. IR spectra were recorded on a Perkin-Elmer 1640 FT-IR spectrometer. Optical rotations were measured on a Perkin-Elmer 343 polarimeter. Mass spectra were recorded on WATERS Micro-mass ZQ 4000 (ESI Probe) spectrometer. Melting points are uncorrected and recorded on Buchi B-540 melting point apparatus. Column chromatography was performed with Merck silica gel (100-200 mesh) and preparative TLC was carried out on plates prepared with Merck Silica gel G. Moisture sensitive reactions were conducted under a dry nitrogen atmosphere. All solvents were distilled at their boiling point, and other commercially available reagents were used as received, unless otherwise stated.

Synthesis of the Known Aldehyde 1:

The aldehyde 1 was already prepared from the known 10-deoxoallylartemisinin via ozonolysis (*J. Med. Chem.* 2004, 47, 1290-1298), but here we have synthesized in one step using $OsO_4$—$NaIO_4$-lutidine reagent system in dioxane-water mixture (*Org. Lett* 2004, 3217-3219) for the first time. The preparation of aldehyde in one step process has been done for the first time using $OsO_4$—$NaIO_4$-lutidine reagent system in dioxane-water mixture.

Procedure: To a solution of 10-deoxoallylartemisinin (1.0 g, 3.246 mmol) in dioxane-water (3:1, 30 mL) were added 2,6-lutidine (0.732 mL, 6.493 mmol), $OsO_4$ (2.5% in 2-methyl-2-propanol, 0.5 mL, 0.049 mmol) and $NaIO_4$ (2.76 g, 12.987 mmol). The reaction was stirred at 28° C. After completion of the reaction (as monitored by TLC), water (35 mL) and $CH_2Cl_2$ (70 mL) were added. The organic layer was separated and the water layer was extracted by $CH_2Cl_2$ (3×30 mL). The combined organic layer was washed with 10% citric acid solution (50 mL), brine (50 mL) and dried over anhydrous $Na_2SO_4$. The solvent was removed, and the product was purified with silica gel (100-200 mesh) column chromatography (eluent 1:4 ethyl acetate:hexane) to afford the known aldehyde (0.610 g, 60%) as white solid.

Compound of Formula (3a)

Compound of formula (3a) was prepared by the reaction of the aldehyde 1 with methyl acrylate under solvent-free condition using 1,4-diazabicyclo[2,2,2]octane as the base.

Procedure: To a mixture of the aldehyde 1 (0.300 g, 0.967 mmol) and methyl acrylate (0.499 g, 5.806 mmol) was added 1,4-diazabicyclo[2,2,2]octane (0.054 g, 0.483 mmol) at 0° C. and the reaction mixture was stirred at 30° C. for three days. After completion of the reaction (as monitored by TLC), the excess methyl acrylate was removed under rota vapor and the crude material was purified by column chromatography over 100-200 mesh silica gel (eluent 1:4 ethyl acetate:hexane) to afford the major diastereomer (0.120 g, 31%) as gummy liquid.

$[\alpha]_D^{20}$=+69.5 (c 1, $CHCl_3$)

IR (neat): ν 3458, 2950, 2875, 1715, 1483, 1378, 1125, 1092, 1013, 877, 825 $cm^{-1}$.

$^1$H NMR ($CDCl_3$, 300 MHz): δ 0.82 (d, J=7.4 Hz, 3H), 0.95 (d, J=5.3 Hz, 3H), 1.41 (s, 3H), 1.20-2.07 (m, 12H), 2.33 (dt, J 3.4, 12.4 Hz, 1H), 2.65 (sextet, 1H), 3.33 (d, J=7.0 Hz, 1H, OH), 3.77 (s, 3H), 4.48 (dd, J 6.3, 11.0 Hz, 1H), 4.77 (br s, 1H), 5.36 (s, 1H), 6.02 (s, 1H), 6.33 (5, 1H).

$^{13}$C NMR ($CDCl_3$, 75 MHz): 12.7, 19.9, 24.3, 24.4, 25.7, 29.6, 33.9, 34.0, 36.2, 37.1, 44.0, 51.5, 51.9, 68.5, 71.6, 80.6, 88.6, 103.0, 125.3, 141.8, 166.4.

ESIMS: 398.3 $[M+2]^+$

Compound of Formula (3b and 3b')

Compound of formula (3b) was prepared by the reaction of the aldehyde 1 with acrylonitrile under solvent-free condition using 1,4-diazabicyclo[2,2,2]octane as a base.

Procedure: To a mixture of the aldehyde 1 (0.300 g, 0.967 mmol) and acrylonitrile (0.512 g, 9.67 mmol) was added 1,4-diazabicyclo[2,2,2]octane (0.054 g, 0.483 mmol) at 0° C. and the reaction mixture was stirred 30° C. for two days. After completion of the reaction (as monitored by TLC), the excess acrylonitrile was removed under rota vapor and the crude material was purified by column chromatography over 100-200 mesh silica gel (eluent 1:9 ethyl acetate:hexane) to separate the two diastereomers 3b (0.142 g, 40%) and 3b' (0.095 g, 27%).

Compound 3b—α Isomer (Solid)

Mp: 137-139° C.

$[\alpha]_D^{20}$=+13.2 (c 1.1, $CHCl_3$)

IR (neat): ν 3469, 2926, 2875, 2225, 1624, 1452, 1378, 1124, 1094, 1041, 944, 877 $cm^{-1}$.

$^1$H NMR ($CDCl_3$, 300 MHz): δ 0.88 (d, J=7.4 Hz, 3H), 0.96 (d, J=4.2 Hz, 3H), 1.40 (s, 3H), 1.15-2.07 (m, 12H), 2.32 (dt, J 3.4, 12.4 Hz, 1H), 2.66 (sextet, 1H), 4.38 (br s, 1H, OH), 4.45 (m, 1H), 4.66 (m, 1H), 5.37 (s, 1H), 6.00 (s, 1H), 6.14 (s, 1H).

$^{13}$C NMR ($CDCl_3$, 75 MHz): 11.6, 12.4, 20.0, 24.7, 25.9, 30.6, 35.5, 36.4, 37.5, 43.4, 51.7, 73.1, 74.8, 80.9, 89.6, 103.1, 125.7, 129.9, 144.1, 188.26.

ESIMS: 386.3 $(M+Na)^+$

Compound 3b'-β isomer (gummy)

$[\alpha]_D^{20}$=+33.0 (c 1.0, $CHCl_3$)

IR (neat): ν 3468, 2925, 2879, 2224, 1449, 1377, 1119, 1093, 1051, 1014, 943 $cm^{-1}$.

$^1$H NMR ($CDCl_3$, 300 MHz): δ 0.87 (d, J=7.4 Hz, 3H), 0.96 (d, J=5.2 Hz, 3H), 1.66 (s, 3H), 1.25-2.17 (m, 12H), 2.32 (dt, J 3.4, 12.4 Hz, 1H), 2.66 (sextet, 1H), 3.63 (br s, 1H, OH), 4.59 (m, 2H), 5.37 (s, 1H), 6.09 (s, 1H), 6.24 (s, 1H).

$^{13}$C NMR ($CDCl_3$, 75 MHz): δ 12.7, 20.1, 24.7, 25.9, 30.0, 33.3, 34.2, 36.5, 37.5, 43.8, 51.9, 70.0, 70.9, 80.8, 89.3, 103.2, 122.0, 130.5, 133.0, 190.5.

ESIMS: 365.3 $[M+2]^+$

Compound of Formula (3c)

Compound of formula (3c) was prepared by the reaction of the aldehyde 1 with methyl vinyl ketone in dimethyl formamide using imidazole as a base along with L-proline as a cocatalyst.

Procedure: To a stirred solution of the aldehyde 1 (0.150 g, 0.487 mmol) and methyl vinyl ketone (0.101 g, 1.461 mmol) in dimethylformamide (5 mL) were added imidazole (0.019 g, 0.290 mmol) and L-proline (0.033 g, 0.290 mmol).

The reaction mixture was stirred at 30° C. for overnight. After completion of the reaction (as monitored by TLC), the reaction mass was diluted with ethyl acetate (30 mL) and washed with water (2×15 mL). The organic layer was dried over anhydrous $Na_2SO_4$, concentrated and the crude product was purified by preparative TLC (1:5 ethyl acetate:hexane) to afford the major diastereomer (0.110 g, 60%)

$[\alpha]_D^{20}$=14.4 (c 0.45, $CHCl_3$).

IR (neat): ν 3481, 2923, 2852, 1717, 1673, 1434, 1378, 1220, 1129, 1053, 878, 772 $cm^{-1}$.

$^1$H NMR ($CDCl_3$, 300 MHz): δ 0.74 (d, J=7.1 Hz, 3H), 0.95 (d, J=6.0 Hz, 3H), 1.38 (s, 3H), 1.20-2.20 (m, 13H), 2.31 (m, 1H), 2.36 (s, 3H, -Me), 3.77 (t, J=6.5 Hz, 1H), 4.49 (brs, 1H, —OH), 4.78 (d, J=9.0 Hz, 1H), 5.29 (s, 1H), 6.18 (s, 1H), 6.30 (s, 1H).

$^{13}$C NMR ($CDCl_3$, 75 MHz): δ 204.5, 188.2, 122, 104.7, 91.8, 80.5, 75, 51.7, 45.9, 37.3, 36.1, 34.0, 30.0, 29.5, 28.4, 25.9, 24.7, 21.2, 20.2, 13.6

ESIMS: m/z 365.3 $[M+2]^+$

Compound of Formula (3d)

Compound of formula (3d) was prepared by the reaction of the aldehyde 1 with 2-cyclohexenone in 1:1 mixture of THF-water using 4-(N,N-dimethylamino)-pyridine as a base.

Procedure: To a solution of the aldehyde 1 (0.112 g, 0.361 mmol) and 2-cyclohexenone (0.034 g, 0.361 mmol) in 1:1 mixture of THF-water (2 mL) was added 4-(N,N-dimethylamino)-pyridine (0.044 g, 0.361 mmol) and the reaction mixture was stirred at 30° C. for overnight. After completion of the reaction (as monitored by TLC), the reaction mass was diluted with ether (30 mL) and washed with water (2×15 mL). The washings were further extracted with ethyl acetate (3×15 mL). The combined organic layer was dried over anhydrous $Na_2SO_4$, concentrated and the crude product was purified by column chromatography over 100-200 mesh silica gel (eluent 1:9 and 1:6 ethyl acetate:hexane) to afford the major diastereomer (0.074 g, 51%) as solid compound.

Mp: 134-135° C.

$[\alpha]_D^{20}=-3.4$ (c 1.1, CHCl$_3$).

IR (neat): ν 3495, 2924, 2873, 1726, 1667, 1454, 1374, 1223, 1133, 1055, 878, 754 cm$^{-1}$.

$^1$H NMR (CDCl$_3$, 300 MHz): δ 0.92 (d, J=7.3 Hz, 3H), 0.95 (d, J=6.2 Hz, 3H), 1.39 (s, 3H), 1.23-2.04 (m, 15H), 2.39-2.43 (m, 3H), 2.68 (m, 1H), 3.72 (m, 1H), 4.13 (q, J=7.1 Hz, 1H), 4.27 (br s, 1H), 4.99 (d, J=9.8 Hz, 1H), 5.23 (s, 1H), 7.18 (t, J 3.8 Hz, 1H).

$^{13}$C NMR (CDCl$_3$, 75 MHz): δ 13.5, 20.2, 21.2, 22.8, 24.8, 25.7, 26.0, 29.5, 34.1, 36.0, 37.4, 38.0, 38.6, 45.8, 51.6, 65.4, 73.9, 80.8, 91.8, 104.4, 141.3, 145.6, 199.3.

ESIMS: 410.0 [M+4]$^+$

Compound of Formula (3e and 3e')

Compound of formula (3e and 3e') was prepared by the reaction of the aldehyde 1 with 2-cyclopentenone in 1:1 mixture of THF-water using 4-(N,N-dimethylamino)-pyridine as a base.

Procedure: To a solution of the aldehyde 1 (0.130 g, 0.419 mmol) and 2-cyclopentenone (0.034 g, 0.419 mmol) in 1:1 mixture of THF-water (2 mL) was added 4-(N,N-dimethylamino)-pyridine (0.051 g, 0.419 mmol) and the reaction mixture was stirred 30° C. for overnight. After completion of the reaction (as monitored by TLC), the reaction mass was diluted with ether (30 mL) and washed with water (2×15 mL). The washings were further extracted with ethyl acetate (3×15 mL). The combined organic layer was dried over anhydrous Na$_2$SO$_4$, concentrated and the crude product was purified by preparative TLC (1:2 ethyl acetate:hexane) to separate two diastereomers 3e (0.065 g, 40%) and 3e' (0.032 g, 20%).

Compound 3e—α Isomer (Upper)

$[\alpha]_D^{20}=-17.1$ (c 0.5, CHCl$_3$).

IR (neat): ν 3469, 2918, 2849, 1726, 1697, 1432, 1378, 1226, 1129, 1054, 925, 875 cm$^{-1}$.

$^1$H NMR (CDCl$_3$, 300 MHz): δ 0.89 (d, J=7.1 Hz, 3H), 0.91 (d, J=5.8 Hz, 3H), 1.39 (s, 3H), 1.25-2.03 (m, 13H), 2.17-2.42 (m, 3H) 2.43-2.60 (m, 2H), 335 (m, 1H), 4.27 (m, 1H), 4.88 (d, J=9.3 Hz, 1H), 5.23 (s, 1H), 7.65 (s, 1H).

$^{13}$C NMR (CDCl$_3$, 75 MHz): δ 13.6, 20.2, 21.2, 24.7, 26.0, 26.5, 29.6, 34.1, 35.5, 36.0, 36.7, 37.4, 45.7, 51.6, 64.5, 73.7, 80.8, 91.8, 104.4, 148.5, 158.5, 208.9.

ESIMS: 415.8 [M+Na]$^+$

Compound 3e'-β Isomer (Lower)

$[\alpha]_D^{20}=+22.7$ (c 0.7, CHCl$_3$).

IR (neat): ν 3436, 2918, 2849, 1696, 1450, 1377, 1219, 1127, 1052, 876, 772 cm$^{-1}$.

$^1$H NMR (CDCl$_3$, 300 MHz): δ 0.84 (d, J=7.3 Hz, 3H), 0.91 (d, J=5.8 Hz, 3H), 1.39 (s, 3H), 1.25-2.16 (m, 13H), 2.30 (dt, J 3.4, 12.4 Hz, 1H), 2.44 (m, 1H), 2.61-2.67 (m, 3H), 3.41 (d, J=6.1 Hz, 1H), 4.36-4.41 (m, 1H), 4.72 (br s, 1H), 5.37 (s, 1H), 7.63 (s, 1H).

$^{13}$C NMR (CDCl$_3$, 75 MHz): δ 14.0, 20.2, 21.9, 24.6, 26.0, 26.5, 29.9, 34.2, 35.1, 35.6, 36.5, 37.4, 46.2, 52.3, 66.4, 72.2, 81.0, 95.9, 103.4, 148.0, 159.0, 208.8.

ESIMS: 395.1 [M+3]$^+$

We claim:

1. A compound of general formula 3

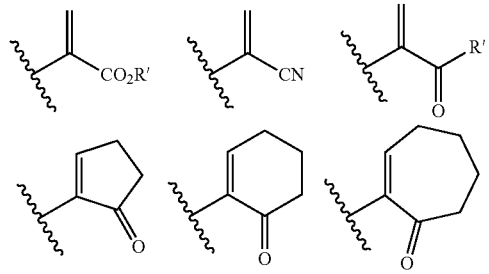

General formula 3 wherein R is selected from:

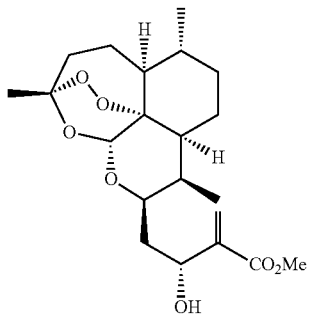

wherein;
R' is methyl, ethyl, i-propyl, t-butyl, or aryl; and
R" is methyl, ethyl, or i-propyl.

2. A compound as claimed in claim 1 wherein the representative compounds of general formula 3 comprising the structural formula 3a to 3e:

Compound 3a

Compound 3b

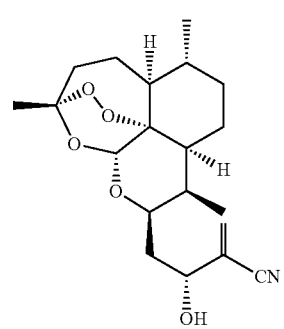

-continued

Compound 3b'

Compound 3c

Compound 3d

Compound 3e

Compound 3e'

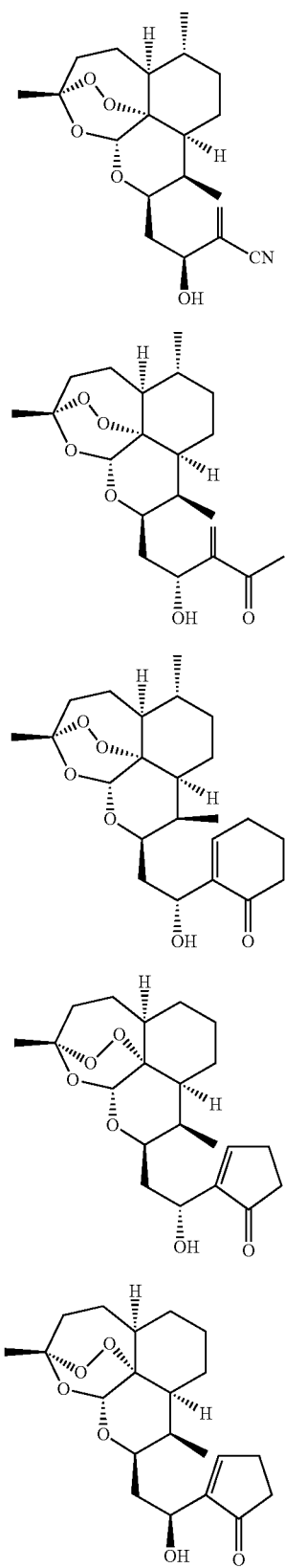

3. A compound as claimed in claim 1 wherein the compounds of general formula 3 are useful as anticancer agents.

4. A process for preparation of compounds of general formula 3 as claimed in claim 1 wherein the process steps comprising:

(i) reacting 10-deoxoallylartemisinin with OsO4-NaIO4, 2,6-lutidine reagent system in dioxane-water at a temperature ranging between 28-30° C. to obtain the compound aldehyde of formula 1, formula 1

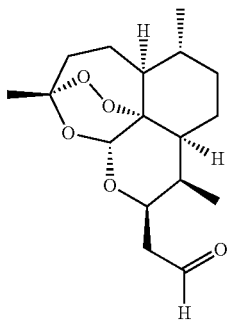

(ii) reacting the compound of formula 1 with an α,β-unsaturated carbonyl compound in presence of a base at a temperature ranging between 0° C. to 40° C. for a period ranging up to 3 days, purifying the desired compound of general formula 3 using chromatographic methods.

5. The process as claimed in claim 4 wherein the α,β-unsaturated carbonyl compound is selected from a group consisting of methyl acrylate, acrylonitrile, methyl vinyl ketone, 2-cycohexenone, 2-cyclopentenone.

6. The process as claimed in claim 4 wherein the base is selected from a group consisting of 1,4-diazabicyclo[2.2.2] octane, imidazole, and 4-(N,N-dimethylamino)-pyridine, wherein if the base is imidazole it is used in combination of with L-proline as a co-catalyst.

7. The process as claimed in claim 4 wherein the reaction can be carried out in absence of solvent or may be carried out in presence of a solvent selected from a group consisting of dimethyl formamide (DMF), 1:1 mixture of THF (tetrahydrofuran)-water.

8. The process as claimed in claim 4 wherein the chromatographic method for purification of the compounds is selected from column chromatography over silica gel of 100-200 mesh and preparative thin layer chromatography (TLC) using silica gel of TLC grade.

9. A pharmaceutical composition comprising an effective amount of at least one compound of general formula 3 as claimed in claim 1 and a pharmaceutically acceptable carrier, diluent or excipients.

* * * * *